(12) United States Patent
Guo

(10) Patent No.: US 12,172,036 B2
(45) Date of Patent: Dec. 24, 2024

(54) ROTATING GANTRY AND RADIOTHERAPY EQUIPMENT

(71) Applicants: OUR UNITED CORPORATION, Xi'an (CN); OUR Innobeam Medical Co., Ltd, Beijing (CN)

(72) Inventor: Zhao Guo, Xi'an (CN)

(73) Assignees: OUR UNITED CORPORATION (CN); OUR Innobeam Medical Co., Ltd (CN)

( * ) Notice: Subject to any disclaimer, the term of this patent is extended or adjusted under 35 U.S.C. 154(b) by 951 days.

(21) Appl. No.: 17/207,231

(22) Filed: Mar. 19, 2021

(65) Prior Publication Data

US 2021/0293373 A1 Sep. 23, 2021

(30) Foreign Application Priority Data

Mar. 20, 2020 (CN) .......................... 202010202789.4

(51) Int. Cl.
*A61N 5/10* (2006.01)
*A61B 6/00* (2006.01)
(Continued)

(52) U.S. Cl.
CPC ............ *A61N 5/1081* (2013.01); *A61B 6/035* (2013.01); *A61B 6/4435* (2013.01);
(Continued)

(58) Field of Classification Search
CPC ....... A61B 6/44; A61B 6/4429; A61B 6/4435; A61B 6/4441; A61B 6/4447; A61B 6/032;
(Continued)

(56) References Cited

U.S. PATENT DOCUMENTS

| 4,132,895 A * | 1/1979 | Froggatt | ................ | A61B 6/032 378/146 |
| 7,010,081 B2 * | 3/2006 | Brunnett | ................ | A61B 6/035 378/4 |

(Continued)

FOREIGN PATENT DOCUMENTS

| CN | 1785454 | 6/2006 |
| CN | 201564993 | 9/2010 |

(Continued)

*Primary Examiner* — Allen C. Ho
(74) *Attorney, Agent, or Firm* — Emerson, Thomson & Bennett, LLC; Roger D. Emerson; Matt J. Wilson

(57) ABSTRACT

A rotating gantry and radiotherapy equipment are provided. The rotating gantry includes a fixed support frame, a bearing, a roller, and at least two support components, a bearing outer ring of the bearing is connected to the fixed support frame, a bearing inner ring of the bearing is connected to one end of the roller, and the support components support the roller and roll relatively to the roller. Therefore, an embodiment of the present disclosure adopts a dual support of the support components and the bearing, improves a support rigidity and rotation accuracy of the roller, and makes efficient and accurate treatment possible. The rotating gantry in an embodiment of the present disclosure has an integral structure with small axial space, may easily pass through a narrow hospital labyrinth, is flexible in transportation and convenient in installation.

20 Claims, 6 Drawing Sheets

(51) Int. Cl.
*A61B 6/03* (2006.01)
*F16M 11/10* (2006.01)
*F16H 1/16* (2006.01)
*F16H 7/02* (2006.01)

(52) U.S. Cl.
CPC ............. *F16M 11/105* (2013.01); *F16H 1/16* (2013.01); *F16H 7/02* (2013.01)

(58) Field of Classification Search
CPC .. A61B 6/035; A61N 5/10; A61N 2005/1054; A61N 2005/1061; A61N 5/1077; A61N 5/1081
USPC ................. 378/15, 62, 63, 65, 189, 196–198
See application file for complete search history.

(56) References Cited

U.S. PATENT DOCUMENTS

| | | | |
|---|---|---|---|
| 7,381,979 B2* | 6/2008 | Yamashita | A61N 5/1081 250/492.23 |
| 8,101,933 B2* | 1/2012 | Aoi | A61N 5/10 378/65 |
| 8,170,175 B2* | 5/2012 | Kasuya | A61B 6/035 378/15 |
| 8,662,757 B2* | 3/2014 | Zhang | A61B 6/44 384/549 |
| 9,974,496 B2* | 5/2018 | Liu | A61N 5/1049 |
| 9,974,980 B2* | 5/2018 | Liu | A61N 5/1081 |
| 10,143,860 B2* | 12/2018 | Tsumoto | A61N 5/01 |
| 10,371,232 B2* | 8/2019 | Bergfjord | A61B 6/4435 |
| 10,441,816 B2* | 10/2019 | Liu | A61B 6/4435 |
| 11,229,409 B2* | 1/2022 | Deutschmann | A61B 6/462 |

FOREIGN PATENT DOCUMENTS

| | | |
|---|---|---|
| CN | 101854864 A | 10/2010 |
| CN | 101854864 B | 3/2013 |
| CN | 203663251 | 6/2014 |
| CN | 105413070 | 3/2016 |

* cited by examiner

ROTATING GANTRY AND RADIOTHERAPY EQUIPMENT

CROSS-REFERENCE TO RELATED APPLICATIONS

The present application claims priority to Chinese application No. 202010202789.4, filed on Mar. 20, 2020, and entitled "Rotating Gantry and Radiotherapy Equipment", the entire contents of which are hereby incorporated by reference.

TECHNICAL FIELD

Embodiments of the present disclosure relate to the field of medical technology, in particular to a rotating gantry and radiotherapy equipment.

BACKGROUND

Rotating gantry is one of the key parts of large-scale radiotherapy equipment. Rotating gantry has the characteristics of large structure and high accuracy. The principle of the rotating gantry is: if only one irradiation direction is used in radiotherapy, normal cells between the skin and a tumor have to receive at least one third of a tumor radiation dose, resulting in varying degrees of damage. In order to reduce this part of damage and increase a coke to skin ratio in the treatment, it is required to irradiate from different directions in a treatment process, and divide a total dose into a plurality of radiation directions, so that a dose to normal tissues is greatly reduced. The role of the rotating gantry is a mechanical structure that supports a radiation beam of radiotherapy to irradiate a lesion from different angles.

A typical rotating gantry adopts a C-arm structure. This large cantilever structure has a small slewing bearing, resulting in an inability to increase rotation speed, weak support rigidity, and low slewing accuracy, which is difficult to meet the accuracy and efficiency required for modern accuracy radiotherapy. While a rotating gantry using a roller structure is dual-supported and has to be transported separately, which increases delivery time. At the same time, due to a large base size, an axial size of the whole machine is affected, occupying more space.

SUMMARY

In view of the this, the technical problem solved by embodiments of the present disclosure is to provide a rotating gantry and radiotherapy equipment to overcome all or part of the problems of radiotherapy equipment in the prior art.

An embodiment of the present disclosure provides a rotating gantry, including: a fixed support frame, a bearing, a roller, and at least two support components, a bearing outer ring of the bearing being connected to the fixed support frame, a bearing inner ring of the bearing being connected to one end of the roller, and the support components supporting the roller and rolling relatively to the roller.

According to a second aspect of the present disclosure, an embodiment of the present disclosure provides a rotating gantry, including: a fixed support frame, a bearing, a roller, and at least one support component, a bearing outer ring of the bearing being connected to the fixed support frame, a bearing inner ring of the bearing being connected to one end of the roller, and the support component supporting the roller and rolling relatively to the roller.

According to another aspect of the present disclosure, an embodiment of the present disclosure provides a radiotherapy equipment that uses any one of the above rotating gantry.

The rotating gantry according to an embodiment of the present disclosure includes a fixed support frame, a bearing, a roller, and at least two support components, a bearing outer ring of the bearing is connected to the fixed support frame, a bearing inner ring of the bearing is connected to one end of the roller, and the support components support the roller and roll relatively to the roller. Therefore, an embodiment of the present disclosure adopts a dual support of the support components and the bearing, improves a support rigidity and rotation accuracy of the roller, and makes efficient and accurate treatment possible. The rotating gantry in an embodiment of the present disclosure has an integral structure with small axial space, may easily pass through a narrow hospital labyrinth, is flexible in transportation and convenient in installation.

BRIEF DESCRIPTION OF THE DRAWINGS

In order to more clearly illustrate the technical solution in embodiments of the present disclosure or the prior art, the following will briefly introduce the accompanying drawings that need to be used in the description of the embodiments or the prior art. Obviously, the accompanying drawings in the following description are only some of the embodiments described in the embodiments of the present disclosure. For those of ordinary skill in the art, other accompanying drawings may also be obtained based on these accompanying drawings.

Figure 1:
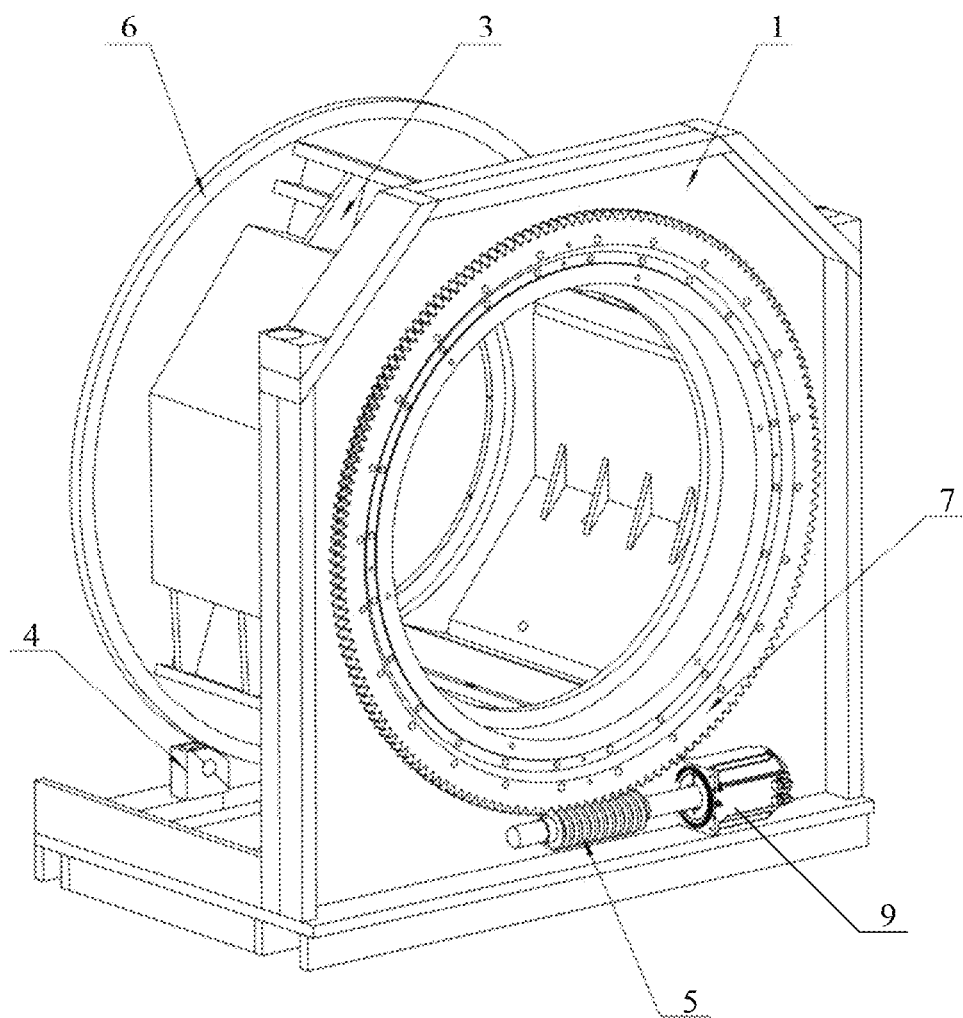
FIG. 1 is a schematic structural diagram of a rotating gantry according to an embodiment of the present disclosure.

The reference numerals respectively indicate:
1-Fixed support frame, 2-bearing, 3-roller, 4-support component, 401-box, 402-support shaft, 403-cam bearing, 5-involute worm, 6-guide rail, 7-gear ring, 8-conductive slip ring, 9-drive motor, 10-transmission wheel, 101-protrusion, 11-transmission belt.

DETAILED DESCRIPTION OF EMBODIMENTS

In order to make those skilled in the art better understand the technical solution in the embodiments of the present disclosure, the technical solution in the embodiments of the present disclosure will be clearly and completely described below in conjunction with the accompanying drawings in the embodiments of the present disclosure. Obviously, the described embodiments are only part of the embodiments of the present disclosure, rather than all the embodiments.

Based on the embodiments in the embodiments of the present disclosure, all other embodiments obtained by those of ordinary skill in the art should fall within the protection scope of the embodiments of the present disclosure.

Figure 2:
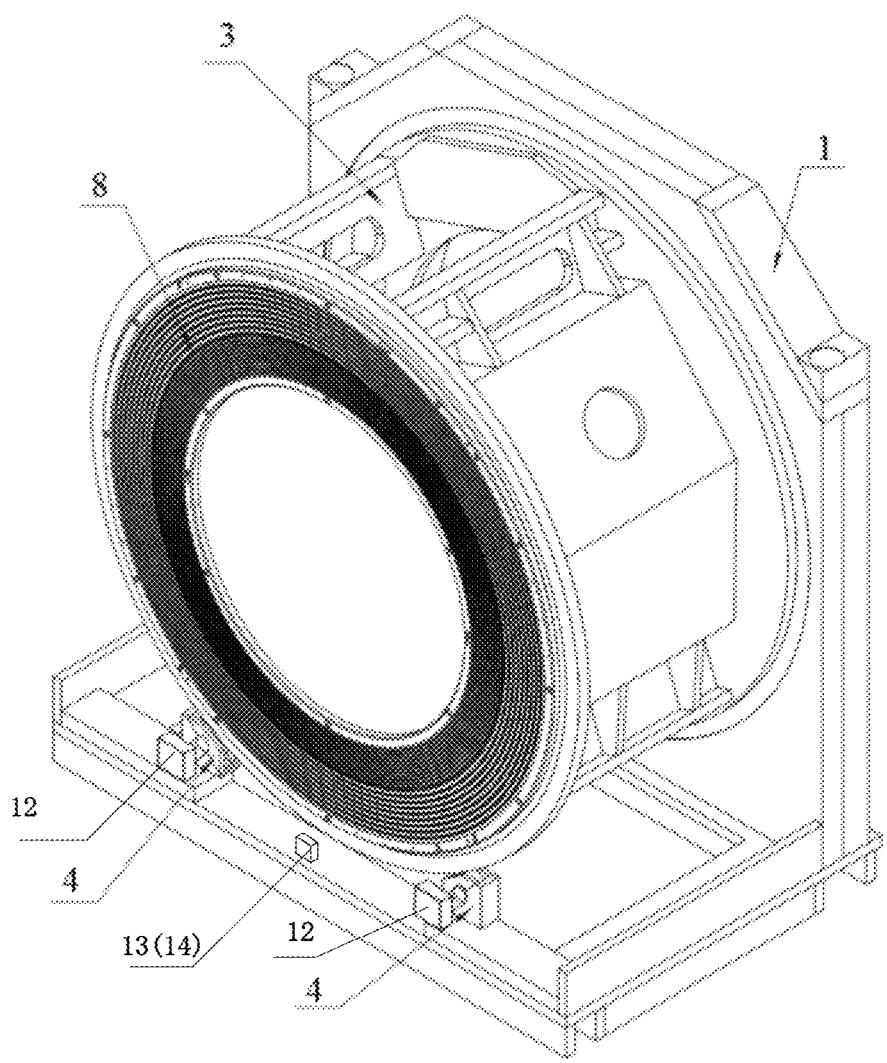
FIG. 2 is a schematic structural diagram of a rotating gantry in another direction according to an embodiment of the present disclosure.
Figure 3:
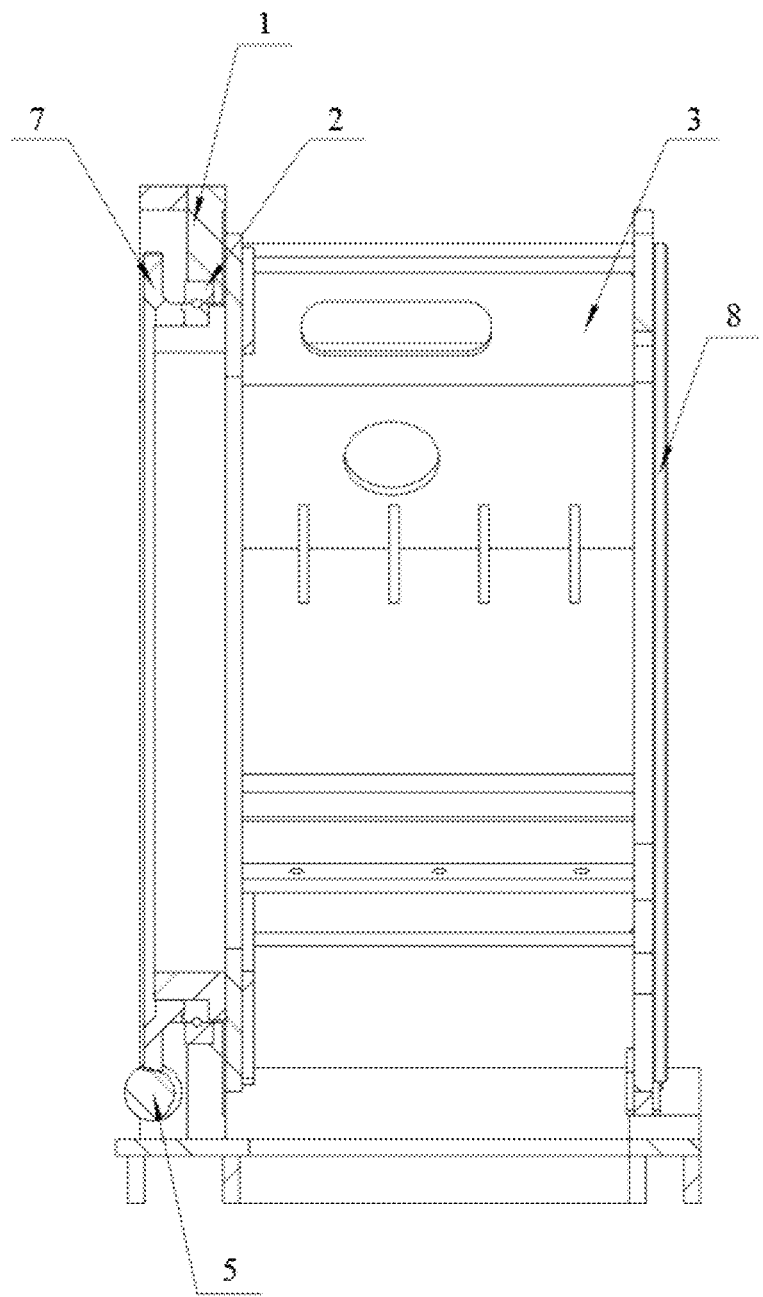
FIG. 3 is a longitudinal cross-sectional view of a rotating gantry according to an embodiment of the present disclosure.

As shown in FIG. 1 to FIG. 3, according to an embodiment of the present disclosure, a rotating gantry includes: a fixed support frame 1, a bearing 2, a roller 3, and at least two support components 4, a bearing outer ring of the bearing 2 is connected to the fixed support frame 1, a bearing inner ring of the bearing 2 is connected to one end of the roller 3, and the support components 4 support the roller 3 and roll relatively to the roller 3.

The bearing 2 is disposed between the roller 3 and the fixed support frame 1, and the roller 3 may rotate relative to the fixed support frame 1 under the action of the first drive unit. At the same time, the bearing 2 is fixed by the fixed support frame 1 to support the roller 3. By providing the at least two support components 4, the support components 4 may support the roller 3 under the premise of ensuring that no additional resistance is generated. Combining a common support function of the bearing 2 and the support components 4, a support rigidity and rotation accuracy of the roller 3 are improved, making efficient and accurate treatment possible. At the same time, the support components 4 are small in size and are disposed under the roller 3, and do not exceed an axial range of the roller 3. The rotating gantry has an integral structure with small axial space, may easily pass through a narrow hospital labyrinth, is flexible in transportation and convenient in installation.

Figure 4:
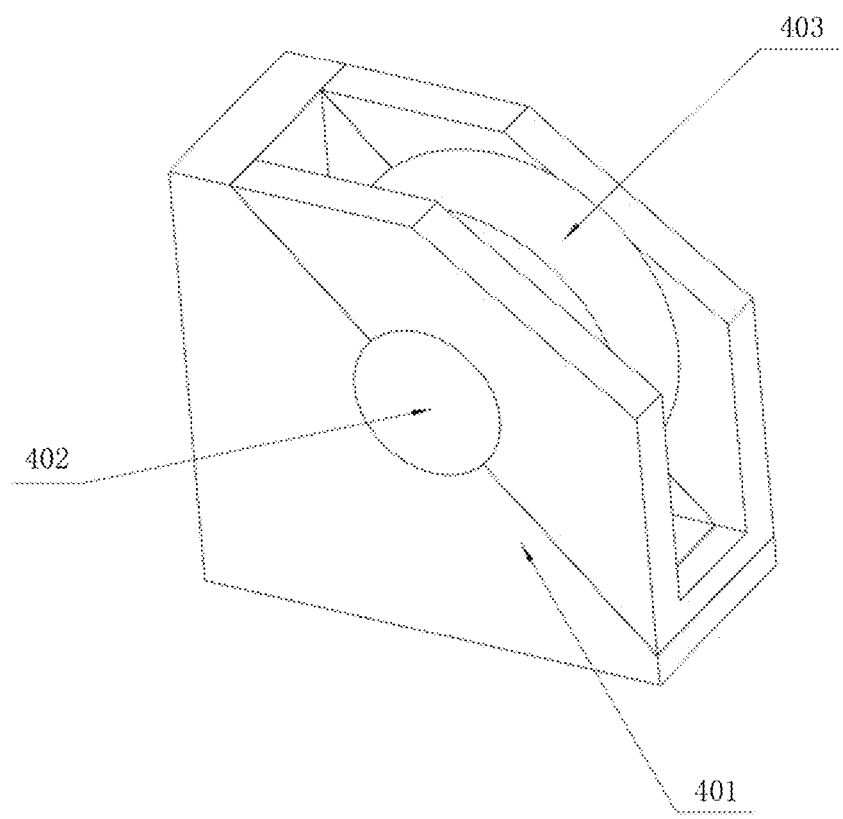
FIG. 4 is a schematic structural diagram of a support component of a rotating gantry according to an embodiment of the present disclosure.

For example, in an embodiment of the present disclosure, in order to realize rolling contact between the support components 4 and the roller 3 and high-rigidity support, as shown in FIG. 4, the support components 4 include a box 401, a support shaft 402, and a cam bearing 403, the box 401 is connected to the fixed support frame 1, the support shaft 402 is fixed in the box 401, the support shaft 402 is connected to a bearing inner ring of the cam bearing 403, and a bearing outer ring of the cam bearing 403 is tangent to an other end of the roller 3 and rolls relatively to the other end of the roller 3. The box 401 is connected to the fixed support frame 1 to realize fixation of the support components 4 in the rotating gantry. The cam bearing 403 is installed on the box 401 through the support shaft 402, and the box 401 can limit an axial movement of the cam bearing 403. The cam bearing 403 is in contact with the roller 3 through its bearing outer ring. When the roller 3 rotates, the bearing outer ring of the cam bearing 403 rotates accordingly, and the two roll relatively. Through the support components 4, an effect of resistance-free support is achieved. At the same time, improving the support rigidity and ensuring the rotation accuracy of the rotating gantry are prerequisites for providing high-speed rotation, which meet the accuracy and efficiency required for modern accurate radiotherapy.

At the same time, the support components 4 are small in size, do not affect an axial size of the whole machine, and occupy a small space, so that the gantry has an integral structure with small axial space, and may easily pass through a narrow hospital labyrinth, is flexible in transportation and convenient in installation.

For example, in an embodiment of the present disclosure, in order to reduce structural complexity of the roller 3 and reduce the processing difficulty, the other end of the roller 3 is provided with a guide rail 6, and the bearing outer ring of the cam bearing 403 is tangent to the other end of the roller 3 and rolls relatively to the other end of the roller 3 through the guide rail 6. In order to realize the relative rolling between the roller 3 and the support components 4, an outer circumference of the roller 3 needs to have a circle of circular structure for tangential contact with the support components 4. The guide rail 6 is installed at one end of the roller 3, and the guide rail 6 is in contact with the bearing outer ring of the cam bearing 403. The guide rail 6 is tangent to the bearing outer ring of the cam bearing 403 and rolls relatively to the bearing outer ring of the cam bearing 403, realizing resistance-free support of the support components to the roller 3.

In the present embodiment, it is not necessary to change an overall structure of the roller 3, and the guide rail 6 may be installed on an end surface of the roller 3 through fixed connection, so that the above requirement of tangential contact is achieved through a split connection. The size and structural complexity of the overall structure of the roller 3 are reduced, and the processing difficulty and processing cost are reduced accordingly. The problem of processing cost caused by the size of the structure and the processing difficulty is solved.

In the above plurality of embodiments, the roller 3 may be a typical cylinder or an integrally formed structure. The roller 3 may also include a structure such as side plate or flange. The specific structure of the roller 3 does not affect a support effect of the support components 4.

For example, in an embodiment of the present disclosure, in order to improve stability of the roller 3 during rotation, the bearing outer ring of the cam bearing 403 is a circular arc surface adapted to the guide rail 6. An outer ring shape of the guide rail 6 is a concave arc surface or a groove. The bearing outer ring of the cam bearing 403 is adapted to be designed as a circular arc surface, on the one hand, a contact area between the guide rail 6 and the cam bearing 403 is increased to ensure that a support area of the support components 4 to the guide rail 6 is maximized, and the support effect of the support components 4 is ensured, which is beneficial to improve the stability of the roller 3 during the rotation.

On the other hand, the adapted arc surface design of the guide rail 6 and the bearing outer ring of the cam bearing 403 may guide the bearing outer ring of the cam bearing 403 to be tangent to the guide rail 6, and limit an axial position of the cam bearing 403, while ensuring an axial direction of the cam bearing 403 to be parallel to an axial direction of the roller 3.

Therefore, under the premise of ensuring a maximum contact support area and the axial direction parallel, the support components 4 realize high-strength and resistance-free support to the roller 3, and at the same time, the roller 3 rotates relatively and without resistance.

For example, in an embodiment of the present disclosure, in order to ensure a relative rolling effect between the support components 4 and the roller 3 and the support strength of the support components 4, the bearing outer ring of the cam bearing 403 may rotate freely 360 degrees relative to the support shaft 402. Through an interference fit or fixed connection between the support shaft 402 and the bearing inner ring of the cam bearing 403, it is ensured that the support shaft 402 and the bearing inner ring are relatively stationary. After being fixed to the box 401 through the support shaft 402, the bearing outer ring of the cam bearing 403 realizes the 360-degree free rotation with the support shaft 402. When the bearing outer ring of the cam bearing 403 may rotate freely, the roller 3 or the guide rail 6 can roll relative to the bearing outer ring of the cam bearing 403.

At the same time, through the connection relationship between the support shaft 402 and the cam bearing 403, the bearing inner ring of the cam bearing 403 is stationary relative to the support shaft 402, and the support shaft 402 is fixed to the box 401. An overall structure of the support components 4 is stable without loosening. When the roller 3 rotates, the support effect of the support components 4 and the roller 3 or the guide rail 6 is ensured. Under the premise of high rigidity support, the roller 3 can realize stable rotation.

For example, in an embodiment of the present disclosure, in order to provide the support effect of the support components 4 and improve simplicity of an overall structure of the rotating gantry, as shown in FIG. 2, the support components 4 is an even number and are symmetrically arranged on both sides of an axis of the roller 3. In order to realize stable support of the roller 3, a resultant force of the plurality of support components 4 to the roller 3 is vertical upward. To improve the overall simplicity of the rotating gantry and simplify structural complexity, it is best to arrange an even number of support components 4 symmetrically. For an odd number of support components 4 to realize a vertical upward resultant force, it is necessary to have very high requirements on a processing accuracy and installation accuracy of the support components 4, which undoubtedly increases the processing cost and installation difficulty.

In the present embodiment, by symmetrically arranging the support components 4, it can be ensured that the resultant force is vertical upright and balanced with the gravity of the roller 3, and the stability of the support to the roller 3 is the best. At the same time, the symmetrical arrangement only needs to ensure that height sizes of two support components 4 at a symmetrical position are the same. At an installation position, positioning installation may be completed by tangent to the roller 3 or the guide rail 6, the installation difficulty is low. Furthermore, the symmetrical arrangement can ensure the simplicity of the structure and improve aesthetics.

Obviously, under the condition that the processing accuracy and installation accuracy of the support components 4 are satisfied, the number of support components 4 in an embodiment of the present disclosure may also be an odd number, which may also meet some requirements in actual use.

For example, in an embodiment of the present disclosure, in order to drive to realize the stable rotation of the roller 3, the rotating gantry further includes a first drive unit and a first transmission mechanism, the first transmission mechanism is connected to the roller 3, and the first drive unit drives the roller 3 to rotate relative to the fixed support frame 1 through the first transmission mechanism. The first drive unit provides power, the first transmission mechanism drives the roller 3 to rotate, and the first transmission mechanism with stable transmission is used for intermediate transmission, which is beneficial to a stable output of the first drive unit.

For example, in an embodiment of the present disclosure, the first drive unit includes a drive motor 9 and a second transmission mechanism, the drive motor 9 is connected to the fixed support frame 1, and the drive motor 9 drives the second transmission mechanism to cooperate with the first transmission mechanism for transmission. By adding the second transmission mechanism, a torque received by the drive motor 9 can be adjusted, a transmission ratio can be adjusted, and a load can be reduced, which is beneficial to a stable output of the drive motor 9. The drive motor 9 directly drives the roller 3 to rotate through the first transmission mechanism, which requires a relatively large torque. The load on the drive motor 9 is large, and a level requirement on the drive motor 9 is high. At the same time, it causes an increase in the cost of the drive motor 9 and a decrease in service life. At the same time, the drive motor 9 is easily affected by power supply and temperature when outputting high power, and a rotation output is unstable. Therefore, the second transmission mechanism is configured to cooperate with the first transmission mechanism to drive the roller 3, which improves the transmission ratio between the drive motor 9 and the roller 3, reduces power required for rotation of the drive motor 9, and helps to improve a transmission accuracy and stability of the drive motor 9.

For example, in an embodiment of the present disclosure, the first transmission mechanism may be a ring gear 7, the second transmission mechanism may be an involute worm 5 or a transmission gear or a transmission rack, the drive motor 9 drives the involute worm 5 or the transmission gear or the transmission rack to rotate, and the drive motor 9 drives the involute worm 5 or the transmission gear or the transmission rack to mesh with the gear ring 7 for transmission. The second transmission mechanism adopts a toothed transmission structure, which cooperates with the gear ring for meshing transmission. The rigid meshing transmission has a stable transmission process and the transmission is controllable.

For example, the ring gear 7 is connected to the bearing inner ring of the bearing 2, and the first drive unit drives the roller 3 to rotate relative to the fixed support frame 1 through the ring gear 7. The ring gear 7 is coaxially connected to the bearing inner ring of the bearing 2. When the first drive unit drives the ring gear 7 to rotate, the ring gear 7 drives the roller 3 to rotate through the bearing inner ring. Through this coaxial arrangement, the ring gear 7 may drive the roller 3 to rotate stably.

For example, at one end of the roller 3, the drive motor 9 stably drives the roller 3 to rotate relative to the fixed support frame through the ring gear 7, and the support components 4 support at the other end of the roller 3. Through stable driving on the one hand and stable support on the other, the roller 3 can realize stable rotation.

In the present embodiment, the second transmission mechanism may be a transmission gear. There is a rigid transmission between the transmission gear and the ring gear 7, and the transmission stability is high. By adjusting a transmission ratio between the transmission gear and the ring gear 7, a transmission load received by the drive motor 9 may be adjusted. According to an actual equipment specification of the drive motor 9, a matching adjustment of the transmission gear and the ring gear 7 may be performed to ensure a transmission stability of the drive motor 9.

In the present embodiment, the second transmission mechanism may also be the involute worm 5. The involute worm 5 is meshed with the ring gear 7 to achieve an effect of the drive motor 9 driving the ring gear 7. The involute worm 5 has the advantages of strong load-bearing capacity, smooth movement, high transmission efficiency, and long life, which can well solve the transmission problems of the conventional synchronous belt and rack.

In the present embodiment, the second transmission mechanism may also be the transmission rack, which can perform stable meshing transmission with the ring gear 7 to ensure that the drive motor 9 stably drives the roller to rotate.

For example, in an embodiment of the present disclosure, in order to control a size of the rotating gantry on the axis of the roller 3, reduce occupied space, and realize convenient transportation of the rotating gantry, an axis of the involute worm 5 and the axis of the roller 3 are arranged perpendicularly. By arranging the axis of the involute worm 5 perpendicular to the axis of the roller 3, the involute worm 5 does not increase space in the axial direction of the roller 3. At the same time, adopting the vertical axis arrangement, the drive motor 9 may be installed on the fixed support frame 1 conveniently, and unnecessary installation structure in the axial direction of the roller 3 is not required, so that the rotating gantry has an integral structure with small axial space, and may easily pass through a narrow hospital labyrinth, is flexible in transportation and convenient in installation.

At the same time, in the present embodiment, the drive motor 9 is fixed on the fixed support frame 1. As there is no additional connection structure between the drive motor 9, the involute worm 5, the ring gear 7, the bearing 2 and the fixed support frame 1, the overall structure is stable, and when the number of connection levels is the smallest, a transmission effect of the drive motor 9 on the roller 3 is the best.

For example, in an embodiment of the present disclosure, in order to ensure the stability of the drive motor 9 during transmission and stable meshing of the involute worm 5 with the ring gear 7, the axis of the involute worm 5 is horizontally arranged along the fixed support frame 1. For the horizontally arranged involute worm 5, when the drive motor 9 rotates the involute worm 5, the involute worm 5 is not prone to shake in a circumferential direction, a meshing effect between the involute worm 5 and the ring gear 7 is the most stable, and the transmission of the drive motor 9 to the ring gear 7 is also the most stable.

For example, in an embodiment of the present disclosure, in order to improve stability of the drive motor 9 under low-speed rotation, the drive motor 9 is a torque motor. The torque motor is a special motor having a large number of poles, which may continue operating at low speeds or even when the motor is locked, without causing damage to the motor. In this operating mode, the motor may provide a stable torque to load. The torque motor may also provide a torque that is opposite to the direction of operation, avoiding the problem of unstable low-speed motion of the conventional servo motor.

Figure 5:
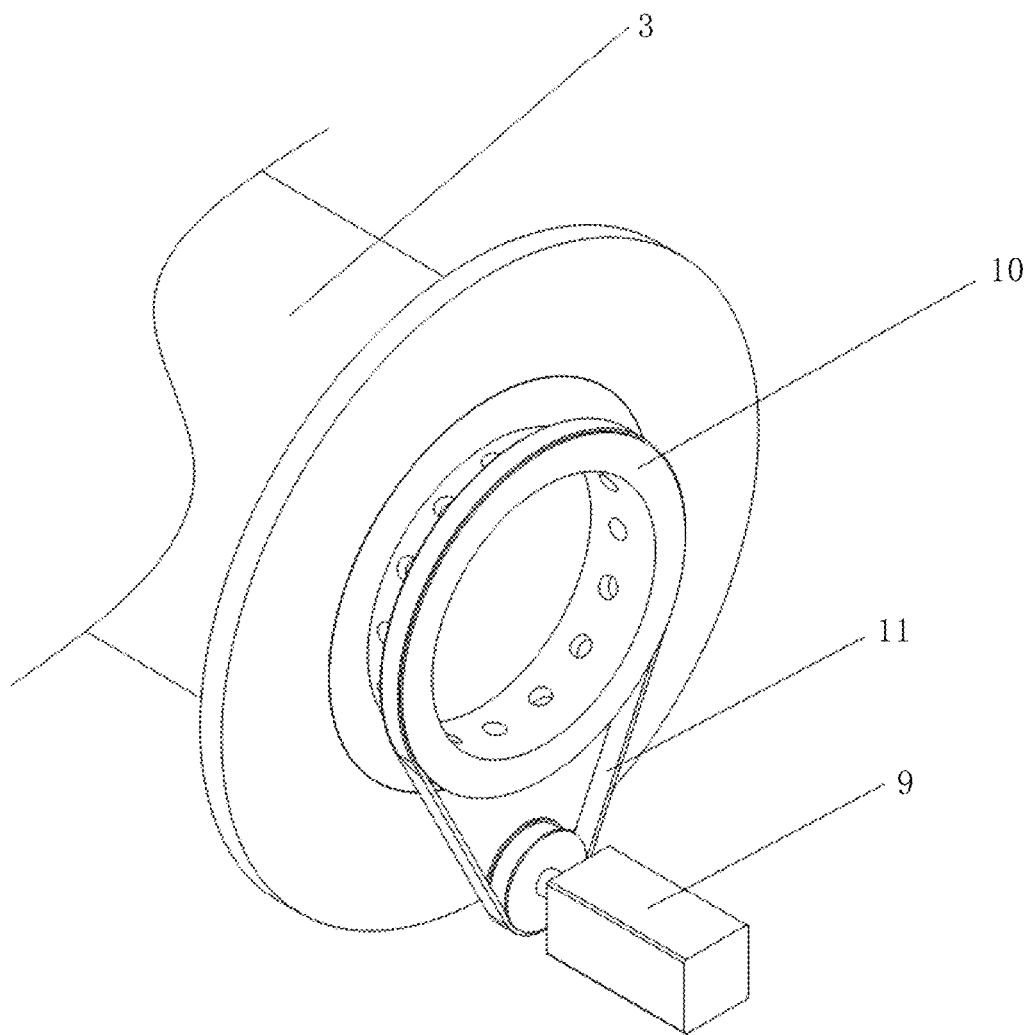
FIG. 5 is a schematic structural diagram of a transmission wheel and a transmission belt of a rotating gantry according to an embodiment of the present disclosure.

For example, as shown in FIG. 5, in an embodiment of the present disclosure, the first transmission mechanism may be a transmission wheel 10, and the second transmission mechanism is a transmission belt 11. According to an actual radiotherapy equipment used by the rotating mechanism, a combined structure of the transmission wheel 10 and the transmission belt 11 may also be adopted. The advantages of the transmission belt 11 method are convenient replacement and low maintenance cost. In the prior art, there are many methods to cooperate the transmission belt 11 with the transmission wheel 10, and it is easy to directly apply the methods in the embodiments of the present disclosure.

Figure 6:
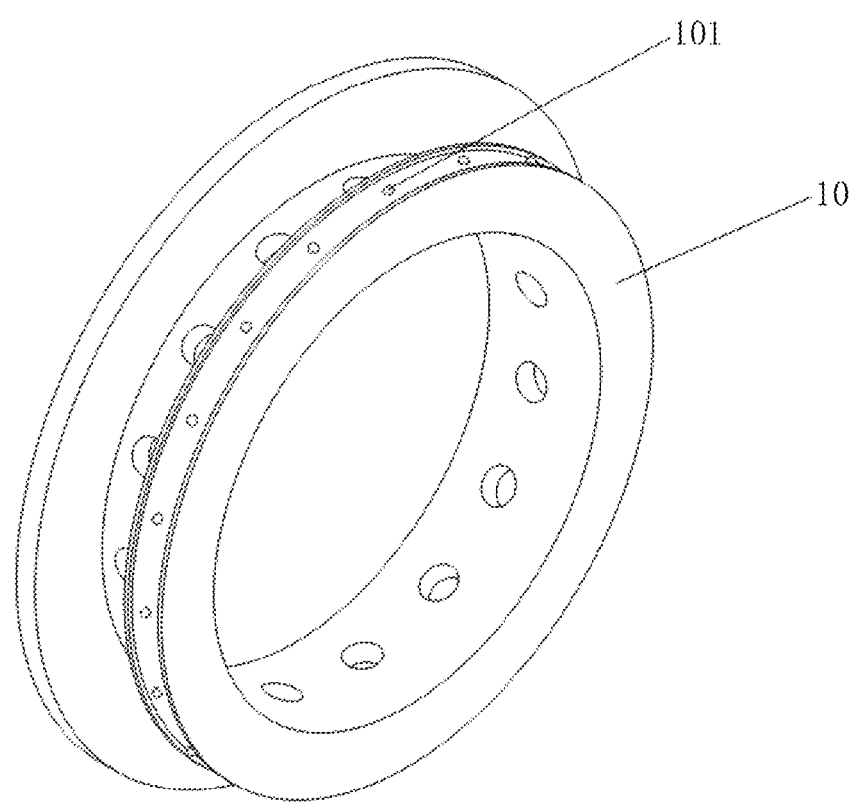
FIG. 6 is a schematic structural diagram of a transmission wheel of a rotating gantry according to an embodiment of the present disclosure.

For example, as shown in FIG. 6, in an embodiment of the present disclosure, the transmission wheel 10 may be provided with a protrusion 101, the transmission belt 11 is provided with a hole, and the protrusion 101 cooperates with the hole for transmission. In order to ensure the stability of the transmission, there will be no slippage between the transmission wheel 10 and the transmission belt 11. By using the cooperation structure of the protrusion 101 and the hole, the transmission wheel 10 and the transmission belt 11 may form a meshing transmission effect similar to that between gears, so as to ensure that there is no slippage occurs during the transmission.

For example, in an embodiment of the present disclosure, the rotating gantry may further include: a second drive unit, where the second drive unit drives the roller 3 to rotate relative to the fixed support frame 1 through the support components 4. A rolling relationship between the support components 4 and the roller 3 may also be used for transmission. The second drive unit drives the support components 4 to rotate, so that in addition to using the first drive unit as a power source of the roller 3, a second power source may be formed, which may operate synchronously with the first drive unit, or may operate separately. When operating synchronously, a load on the first drive unit may be reduced, which is beneficial to the stability of the output of the first drive unit.

For example, in an embodiment of the present disclosure, the second drive unit is arranged on at least one side of the roller 3 and corresponds to the support components 4 respectively. According to an actual use situation, a second drive unit may be provided on each of the support components 4, or may be arranged on one side. According to the power and specification of the second drive unit used, the transmission method may be different, and an arrangement position of the second drive unit is flexible.

For example, in an embodiment of the present disclosure, the second drive unit is a friction drive. The support components 4 use the gravity of the roller 3, and there is a relatively large static friction between the two. By relying on the static friction for transmission, the transmission mechanism between the support components 4 and the roller 3 may be saved, and space occupation may be reduced. The overall structure of the gantry is more compact.

For example, in an embodiment of the present disclosure, in order to realize circuit connection of a radiation unit in the roller 3 during rotation of the rotating gantry, an end surface of the roller 3 away from the bearing 2 is provided with a conductive slip ring 8. The conductive slip ring 8 can provide multi-channel rotation power, data and signal transmission, which greatly simplifies a system structure of the rotating gantry and avoids wire sprain during the rotation. The power and signal transmission between stationary and rotating parts in the gantry is realized through the conductive slip ring 8 fixed on the end surface of the roller 3.

For example, in an embodiment of the present disclosure, the present embodiment also includes a wireless transmitting apparatus and/or a wireless receiving apparatus for signal communication with the conductive slip ring 8, so as to achieve better signal transmission and reception.

For example, in an embodiment of the present disclosure, the rotating gantry further includes a base, and the fixed support frame 1 is fixedly connected to the base. This makes the structural stability of the rotating gantry in the present embodiment better.

For example, in an embodiment of the present disclosure, the supporting components 4 are fixedly connected to the base, thereby further improving the structural stability of the rotating gantry in the present embodiment.

According to a second aspect of the present disclosure, an embodiment of the present disclosure provides a rotating gantry, including: a fixed support frame 1, a bearing 2, a roller 3, and at least one support component 4, a bearing outer ring of the bearing 2 is connected to the fixed support frame 1, a bearing inner ring of the bearing 2 is connected to one end of the roller 3, and the support component 4 supports the roller 3 and rolls relatively to the roller 3.

In the present embodiment, the bearing 2 is disposed between the roller 3 and the fixed support frame 1, and the roller 3 may rotate relative to the fixed support frame 1 under the action of the first drive unit. At the same time, the bearing 2 is fixed by the fixed support frame 1 to support the roller 3. By providing one support component 4, the support component 4 may support the roller 3 under the premise of ensuring that no additional resistance is generated. Combining a common support function of the bearing 2 and the support component 4, a support rigidity and rotation accuracy of the roller are improved, making efficient and accurate treatment possible. At the same time, the support component 4 is small in size and is disposed under the roller 3, and does not exceed an axial range of the roller 3. The rotating gantry has an integral structure with small axial space, may easily pass through a narrow hospital labyrinth, is flexible in transportation and convenient in installation.

Therefore, an embodiment of the present disclosure adopts a dual support of the support components and the bearing, improves a support rigidity and rotation accuracy of the roller, and makes efficient and accurate treatment possible. The rotating gantry in an embodiment of the present disclosure has an integral structure with small axial space, may easily pass through a narrow hospital labyrinth, is flexible in transportation and convenient in installation.

For example, in an embodiment of the rotating gantry of the second aspect of the present disclosure, the support component 4 includes a box 401, a support shaft 402, and a cam bearing 403, the box 401 is connected to the fixed support frame 1, the support shaft 402 is fixed in the box 401, the support shaft 402 is connected to a bearing inner ring of the cam bearing 403, and a bearing outer ring of the cam bearing 403 is tangent to an other end of the roller 3 and rolls relatively to the other end of the roller 3, realizing rolling contact between the support component 4 and the roller 3 and high-rigidity support.

The box 401 is connected to the fixed support frame 1 to realize fixation of the support component 4 in the rotating gantry. The cam bearing 403 is installed on the box 401 through the support shaft 402, and the box 401 can limit an axial movement of the cam bearing 403. The cam bearing 403 is in contact with the roller 3 through its bearing outer ring. When the roller 3 rotates, the bearing outer ring of the cam bearing 403 rotates accordingly, and the two roll relatively. Therefore, through the support component 4, an effect of resistance-free support is achieved. At the same time, improving the support rigidity and ensuring the rotation accuracy of the rotating gantry are prerequisites for providing high-speed rotation, which meet the accuracy and efficiency required for modern accurate radiotherapy.

At the same time, the support component 4 is small in size, does not affect an axial size of the whole machine, and occupies a small space, so that the gantry has an integral structure with small axial space, and may easily pass through a narrow hospital labyrinth, is flexible in transportation and convenient in installation.

For example, in an embodiment of the rotating gantry of the second aspect of the present disclosure, the other end of the roller 3 is provided with a guide rail 6, and the bearing outer ring of the cam bearing 403 is tangent to the other end of the roller 3 and rolls relatively to the other end of the roller 3 through the guide rail 6, which reduces structural complexity of the roller 3 and reduces the processing difficulty.

In order to realize the relative rolling between the roller 3 and the support component 4, an outer circumference of the roller 3 needs to have a circle of circular structure for tangential contact with the support component 4. The guide rail 6 is installed at one end of the roller 3, and the guide rail 6 is in contact with the bearing outer ring of the cam bearing 403. The guide rail 6 is tangent to the bearing outer ring and rolls relatively to the bearing outer ring, realizing resistance-free support of the support component to the roller 3.

Therefore, in the present embodiment, it is not necessary to change an overall structure of the roller 3, and the guide rail 6 may be installed on an end surface of the roller 3 through fixed connection, so that the above requirement of tangential contact is achieved through a split connection. The size and structural complexity of the overall structure of the roller 3 are reduced, and the processing difficulty and processing cost are reduced accordingly. The problem of processing cost caused by the size of the structure and the processing difficulty is solved.

Alternatively, the roller 3 may be a typical cylinder or an integrally formed structure. The roller 3 may also include a structure such as side plate or flange. The specific structure of the roller 3 does not affect a support effect of the support component 4.

Alternatively, in order to improve stability of the roller 3 during rotation, the bearing outer ring of the cam bearing 403 is a circular arc surface adapted to the guide rail 6. An outer ring shape of the guide rail 6 is a concave arc surface or a groove. The bearing outer ring of the cam bearing 403 is adapted to be designed as a circular arc surface, on the one hand, a contact area between the guide rail 6 and the cam bearing 403 is increased to ensure that a support area of the support component 4 to the guide rail 6 is maximized, and the support effect of the support component 4 is ensured, which is beneficial to improve the stability of the roller 3 during the rotation.

On the other hand, the adapted arc surface design of the guide rail 6 and the bearing outer ring of the cam bearing 403 may guide the bearing outer ring of the cam bearing 403 to be tangent to the guide rail 6, and limit an axial position of the cam bearing 403, while ensuring an axial direction of the cam bearing 403 to be parallel to an axial direction of the roller 3. Therefore, under the premise of ensuring a maximum contact support area and the axial direction parallel, the support component 4 realizes high-strength and resistance-free support to the roller 3, and at the same time, the roller 3 rotates relatively and without resistance.

Alternatively, in order to ensure a relative rolling effect between the support component 4 and the roller 3 and the support strength of the support component 4, the bearing outer ring of the cam bearing 403 may rotate freely 360 degrees relative to the support shaft 402. Through an interference fit or fixed connection between the support shaft 402 and the bearing inner ring of the cam bearing 403, it is ensured that the support shaft 402 and the bearing inner ring are relatively stationary. After being fixed to the box 401 through the support shaft 402, the bearing outer ring of the cam bearing 403 realizes the 360-degree free rotation with the support shaft 402. When the bearing outer ring may rotate freely, the roller 3 or the guide rail 6 can roll relative to the bearing outer ring.

At the same time, through the connection relationship between the support shaft 402 and the cam bearing 403, the bearing inner ring of the cam bearing 403 is stationary relative to the support shaft 402, and the support shaft 402 is fixed to the box 401. An overall structure of the support component 4 is stable without loosening. When the roller 3 rotates, the support effect of the support component 4 and the roller 3 or the guide rail 6 is ensured. Under the premise of high rigidity support, the roller 3 can realize stable rotation.

For example, in an embodiment of the rotating gantry of the second aspect of the present disclosure, the rotating gantry further includes a first drive unit and a first transmission mechanism, the first transmission mechanism is connected to the roller 3, and the first drive unit drives the roller 3 to rotate relative to the fixed support frame 1 through the first transmission mechanism.

Therefore, the first drive unit provides power, the first transmission mechanism drives the roller 3 to rotate, and the first transmission mechanism with stable transmission is used for intermediate transmission, which is beneficial to a stable output of the first drive unit, and can also realize the stable rotation of the roller 3.

For example, in an embodiment of the rotating gantry of the second aspect of the present disclosure, the first drive unit includes a drive motor 9 and a second transmission mechanism, the drive motor 9 is connected to the fixed support frame 1, and the drive motor 9 drives the second transmission mechanism to cooperate with the first transmission mechanism for transmission.

Therefore, by adding the second transmission mechanism, a torque received by the drive motor 9 can be adjusted, a transmission ratio can be adjusted, and a load can be reduced, which is beneficial to a stable output of the drive motor 9. The drive motor 9 directly drives the roller 3 to rotate through the first transmission mechanism, which requires a relatively large torque. The load on the drive motor 9 is large, and a level requirement on the drive motor 9 is high. At the same time, it causes an increase in the cost of the drive motor 9 and a decrease in service life. At the same time, the drive motor 9 is easily affected by power supply and temperature when outputting high power, and a rotation output is unstable. Therefore, the second transmission mechanism is configured to cooperate with the first transmission mechanism to drive the roller 3, which improves the transmission ratio between the drive motor 9 and the roller 3, reduces power required for rotation of the drive motor 9, and helps to improve a transmission accuracy and stability of the drive motor 9.

For example, in an embodiment of the rotating gantry of the second aspect of the present disclosure, the first transmission mechanism is a ring gear 7, the second transmission mechanism is an involute worm 5 or a transmission gear or a transmission rack, the drive motor 9 drives the involute worm 5 or the transmission gear or the transmission rack to rotate, and the drive motor 9 drives the involute worm 5 or the transmission gear or the transmission rack to mesh with the gear ring 7 for transmission. The second transmission mechanism adopts a toothed transmission structure, which cooperates with the gear ring for meshing transmission. The rigid meshing transmission has a stable transmission process and the transmission is controllable.

For example, the ring gear 7 is connected to the bearing inner ring of the bearing 2, and the first drive unit drives the roller 3 to rotate relative to the fixed support frame 1 through the ring gear 7. The ring gear 7 is coaxially connected to the bearing inner ring of the bearing 2. When the first drive unit drives the ring gear 7 to rotate, the ring gear 7 drives the roller 3 to rotate through the bearing inner ring. Through this coaxial arrangement, the ring gear 7 may drive the roller 3 to rotate stably.

For example, at one end of the roller 3, the drive motor 9 stably drives the roller 3 to rotate relative to the fixed support frame through the ring gear 7, and the support component 4 supports at the other end of the roller 3. Through stable driving on the one hand and stable support on the other, the roller 3 can realize stable rotation.

In the present embodiment, the second transmission mechanism may be a transmission gear. There is a rigid transmission between the transmission gear and the ring gear 7, and the transmission stability is high. By adjusting a transmission ratio between the transmission gear and the ring gear 7, a transmission load received by the drive motor 9 may be adjusted. According to an actual equipment specification of the drive motor 9, a matching adjustment of the transmission gear and the ring gear 7 may be performed to ensure a transmission stability of the drive motor 9.

In the present embodiment, the second transmission mechanism may also be the involute worm 5. The involute worm 5 is meshed with the ring gear 7 to achieve an effect of the drive motor 9 driving the ring gear 7. The involute worm 5 has the advantages of strong load-bearing capacity, smooth movement, high transmission efficiency, and long life, which can well solve the transmission problems of the conventional synchronous belt and rack.

In the present embodiment, the second transmission mechanism may also be the transmission rack, which can perform stable meshing transmission with the ring gear 7 to ensure that the drive motor 9 stably drives the roller to rotate.

Alternatively, in order to control a size of the rotating gantry on an axis of the roller 3, reduce occupied space, and realize convenient transportation of the rotating gantry, an axis of the involute worm 5 and the axis of the roller 3 are arranged perpendicularly. By arranging the axis of the involute worm 5 perpendicular to the axis of the roller 3, the involute worm 5 does not increase space in the axial direction of the roller 3. At the same time, adopting the vertical axis arrangement, the drive motor 9 may be installed on the fixed support frame 1 conveniently, and unnecessary installation structure in the axial direction of the roller 3 is not required, so that the rotating gantry has an integral structure with small axial space, and may easily pass through a narrow hospital labyrinth, is flexible in transportation and convenient in installation.

At the same time, in the present embodiment, the drive motor 9 is fixed on the fixed support frame 1. As there is no additional connection structure between the drive motor 9, the involute worm 5, the ring gear 7, the bearing 2 and the fixed support frame 1, the overall structure is stable, and when the number of connection levels is the smallest, a transmission effect of the drive motor 9 on the roller 3 is the best.

Alternatively, in order to ensure the stability of the drive motor 9 during transmission and stable meshing of the involute worm 5 with the ring gear 7, the axis of the involute worm 5 is horizontally arranged along the fixed support frame 1. For the horizontally arranged involute worm 5, when the drive motor 9 rotates the involute worm 5, the involute worm 5 is not prone to shake in a circumferential direction, a meshing effect between the involute worm 5 and the ring gear 7 is the most stable, and the transmission of the drive motor 9 to the ring gear 7 is also the most stable.

Alternatively, in order to improve stability of the drive motor 9 under low-speed rotation, the drive motor 9 is a torque motor. The torque motor is a special motor having a large number of poles, which may continue operating at low speeds or even when the motor is locked, without causing damage to the motor. In this operating mode, the motor may provide a stable torque to load. The torque motor may also provide a torque that is opposite to the direction of operation, avoiding the problem of unstable low-speed motion of the conventional servo motor.

For example, in an embodiment of the rotating gantry of the second aspect of the present disclosure, the first transmission mechanism is a transmission wheel 10, and the second transmission mechanism is a transmission belt 11.

According to an actual radiotherapy equipment used by the rotating mechanism, a combined structure of the transmission wheel 10 and the transmission belt 11 may also be adopted. The advantages of the transmission belt 11 method are convenient replacement and low maintenance cost. In the prior art, there are many methods to cooperate the transmission belt 11 with the transmission wheel 10, and it is easy to directly apply the methods in the embodiments of the present disclosure.

For example, in an embodiment of the rotating gantry of the second aspect of the present disclosure, the transmission wheel 10 is provided with a protrusion 101, the transmission belt 11 is provided with a hole, and the protrusion 101 cooperates with the hole for transmission.

In order to ensure the stability of the transmission, there will be no slippage between the transmission wheel 10 and the transmission belt 11. By using the cooperation structure of the protrusion 101 and the hole, the transmission wheel 10 and the transmission belt 11 may form a meshing transmission effect similar to that between gears, so as to ensure that there is no slippage occurs during the transmission.

For example, in an embodiment of the rotating gantry of the second aspect of the present disclosure, the rotating gantry further includes: a second drive unit, where the second drive unit drives the roller 3 to rotate relative to the fixed support frame 1 through the support component 4. A rolling relationship between the support component 4 and the roller 3 may also be used for transmission. The second drive unit drives the support component 4 to rotate, so that in addition to using the first drive unit as a power source of the roller 3, a second power source may be formed, which may operate synchronously with the first drive unit, or may operate separately. When operating synchronously, a load on the first drive unit may be reduced, which is beneficial to the stability of the output of the first drive unit.

Alternatively, the second drive unit 12 is arranged on at least one side of the roller 3 and corresponds to the support component 4. According to an actual use situation, a second drive unit 12 may be provided on a support component 4, or may be arranged on one side. According to the power and specification of the second drive unit 12 used, the transmission method may be different, and an arrangement position of the second drive unit is flexible.

Alternatively, the second drive unit is a friction drive. The support component 4 uses the gravity of the roller 3, and there is a relatively large static friction between the two. By relying on the static friction for transmission, the transmission mechanism between the support component 4 and the roller 3 may be saved, and space occupation may be reduced. The overall structure of the gantry is more compact.

For example, in an embodiment of the rotating gantry of the second aspect of the present disclosure, an end surface of the roller 3 away from the bearing 2 is provided with a conductive slip ring 8. The conductive slip ring 8 can provide multi-channel rotation power, data and signal transmission, which greatly simplifies a system structure of the rotating gantry and avoids wire sprain during the rotation. The power and signal transmission between stationary and rotating parts in the gantry is realized through the conductive slip ring 8 fixed on the end surface of the roller 3.

For example, in an embodiment of the rotating gantry of the second aspect of the present disclosure, the rotating gantry also includes a wireless transmitting apparatus 13 and/or a wireless receiving apparatus 14 for signal communication with the conductive slip ring 8, so as to achieve better signal transmission and reception For example, in an embodiment of the rotating gantry of the second aspect of the present disclosure, the rotating gantry further includes a base, and the fixed support frame 1 is fixedly connected to the base. This makes the structural stability of the rotating gantry in the present embodiment better.

For example, in an embodiment of the rotating gantry of the second aspect of the present disclosure, the supporting component 4 is fixedly connected to the base, thereby further improving the structural stability of the rotating gantry in the present embodiment.

According to another aspect of the present disclosure, a radiotherapy equipment uses the above rotating gantry. By adopting the above rotating gantry, several major problems in the existing radiotherapy equipment are overcome, the support rigidity and rotation accuracy of the roller are improved, making efficient and accurate treatment possible. Therefore, the rotating gantry has an integral structure with small axial space, may easily pass through a narrow hospital labyrinth, is flexible in transportation and convenient in installation.

Of course, implementing any one of the technical solutions of the embodiments of the present disclosure does not necessarily need to achieve all the above advantages at the same time.

Although preferred embodiments of the embodiments of the present disclosure have been described, those skilled in the art may make additional changes and modifications to these embodiments once they learn the basic creative concepts. Therefore, the appended claims are intended to be interpreted as including the preferred embodiments and all the changes and modifications falling within the scope of the embodiments of the present disclosure. Obviously, those skilled in the art may make various changes and modifications to the embodiments of the present disclosure without departing from the spirit and scope of the embodiments of the present disclosure. In this regard, if these modifications and variations of the embodiments of the present disclosure fall within the scope of the claims of the embodiments of the present disclosure and their equivalent technologies, the embodiments of the present disclosure are also intended to include these modifications and variations.

What is claimed is:

1. A rotating gantry, comprising:
a fixed support frame, a bearing, a roller, and at least two support components, a bearing outer ring of the bearing being connected to the fixed support frame, a bearing inner ring of the bearing being connected to one end of the roller, and the at least two support components supporting the roller and rolling relatively to the roller.

2. The rotating gantry according to claim 1, wherein each of the at least two support components comprises a box, a support shaft, and a cam bearing, the box is connected to the fixed support frame, the support shaft is fixed in the box, the support shaft is connected to a bearing inner ring of the cam bearing, and a bearing outer ring of the cam bearing is tangent to an other end of the roller and rolls relatively to the other end of the roller.

3. The rotating gantry according to claim 2, further comprising a guide rail, the other end of the roller is provided with the guide rail, and the bearing outer ring of the cam bearing is tangent to the other end of the roller and rolls relatively to the other end of the roller through the guide rail.

4. The rotating gantry according to claim 1, further comprising a first drive unit and a first transmission mechanism, the first transmission mechanism is connected to the roller, and the first drive unit drives the roller to rotate relative to the fixed support frame through the first transmission mechanism.

5. The rotating gantry according to claim 4, wherein the first drive unit comprises a drive motor and a second transmission mechanism, the drive motor is connected to the fixed support frame, and the drive motor drives the second transmission mechanism to cooperate with the first transmission mechanism for a transmission.

6. The rotating gantry according to claim 5, wherein the first transmission mechanism comprises a ring gear, the second transmission mechanism comprises an involute worm, a transmission gear, or a transmission rack, the drive motor drives the involute worm, the transmission gear, or the transmission rack to rotate, and the drive motor drives the involute worm, the transmission gear, or the transmission rack to mesh with the ring gear for a transmission.

7. The rotating gantry according to claim 5, wherein the first transmission mechanism comprises a transmission wheel, and the second transmission mechanism comprises a transmission belt.

8. The rotating gantry according to claim 7, wherein the transmission wheel comprises a protrusion, the transmission belt comprises a hole, and the protrusion cooperates with the hole for a transmission.

9. The rotating gantry according to claim 1, further comprising a second drive unit, wherein the second drive unit drives the roller to rotate relative to the fixed support frame through the at least two support components.

10. The rotating gantry according to claim 1, further comprising a conductive slip ring, an end surface of the roller away from the bearing is provided with the conductive slip ring.

11. The rotating gantry according to claim 10, further comprising a wireless transmitting apparatus and/or a wireless receiving apparatus for a signal communication with the conductive slip ring.

12. The rotating gantry according to claim 1, wherein the at least two supporting components comprise an odd number of supporting components or an even number of supporting components.

13. A rotating gantry, comprising:
a fixed support frame, a bearing, a roller, and one support component, a bearing outer ring of the bearing being connected to the fixed support frame, a bearing inner ring of the bearing being connected to one end of the roller, and the one support component supporting the roller and rolling relatively to the roller.

14. The rotating gantry according to claim 13, wherein the one support component comprises a box, a support shaft, and a cam bearing, the box is connected to the fixed support frame, the support shaft is fixed in the box, the support shaft is connected to a bearing inner ring of the cam bearing, and a bearing outer ring of the cam bearing is tangent to an other end of the roller and rolls relatively to the other end of the roller.

15. The rotating gantry according to claim 14, further comprising a guide rail, the other end of the roller is provided with the guide rail, and the bearing outer ring of the cam bearing is tangent to the other end of the roller and rolls relatively to the other end of the roller through the guide rail.

16. The rotating gantry according to claim 13, further comprising a first drive unit and a first transmission mechanism, the first transmission mechanism is connected to the roller, and the first drive unit drives the roller to rotate relative to the fixed support frame through the first transmission mechanism.

17. The rotating gantry according to claim 16, wherein the first drive unit comprises a drive motor and a second transmission mechanism, the drive motor is connected to the fixed support frame, and the drive motor drives the second transmission mechanism to cooperate with the first transmission mechanism for a transmission.

18. The rotating gantry according to claim 17, wherein the first transmission mechanism comprises a ring gear, the second transmission mechanism comprise an involute worm, a transmission gear, or a transmission rack, the drive motor drives the involute worm, the transmission gear, or the transmission rack to rotate, and the drive motor drives the involute worm, the transmission gear, or the transmission rack to mesh with the ring gear for a transmission.

19. The rotating gantry according to claim 13, further comprising a second drive unit, wherein the second drive unit drives the roller to rotate relative to the fixed support frame through the one support component.

20. A radiotherapy equipment, comprising: a rotating gantry and a treatment couch, the rotating gantry being configured to carry a part of a radiotherapy apparatus, and the treatment couch being configured to carry a patient;
the rotating gantry comprising a fixed support frame, a bearing, a roller, and one support component, a bearing outer ring of the bearing being connected to the fixed support frame, a bearing inner ring of the bearing being connected to one end of the roller, and the one support component supporting the roller and rolling relatively to the roller.

* * * * *